United States Patent
Manzer

(10) Patent No.: US 6,756,501 B2
(45) Date of Patent: Jun. 29, 2004

(54) MANUFACTURE OF 3-METHYL-TETRAHYDROFURAN FROM ALPHA-METHYLENE-GAMMA-BUTYROLACTONE IN A SINGLE STEP PROCESS

(75) Inventor: Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/191,313

(22) Filed: Jul. 9, 2002

(65) Prior Publication Data

US 2004/0010153 A1 Jan. 15, 2004

Related U.S. Application Data

(60) Provisional application No. 60/304,291, filed on Jul. 10, 2001.

(51) Int. Cl.$^7$ .............................. C07D 307/06
(52) U.S. Cl. ........................................ 549/508
(58) Field of Search ........................................ 549/508

(56) References Cited

U.S. PATENT DOCUMENTS 4,973,717 A * 11/1990 Williams .................... 549/508
5,990,324 A * 11/1999 Takemoto et al. .......... 549/508

FOREIGN PATENT DOCUMENTS

JP  219981  8/1994
JP  217768  8/1996

OTHER PUBLICATIONS

Chemical Abstracts, vol. 121:157510 (1994).*

* cited by examiner

Primary Examiner—Bernard Dentz
(74) Attorney, Agent, or Firm—Inna Y. Belopolsky

(57) ABSTRACT

Disclosed is a single step continuous hydrogenation process for the preparation of 3-methyl-tetrahydrofuran from alpha-methylene-gamma-butyrolactone, in the presence of a catalytic metal.

29 Claims, No Drawings

MANUFACTURE OF 3-METHYL-TETRAHYDROFURAN FROM ALPHA-METHYLENE-GAMMA-BUTYROLACTONE IN A SINGLE STEP PROCESS

This application claims priority from Provisional Application 60/304,291 filed Jul. 10, 2001.

FIELD OF INVENTION

Described is a continuous process comprising a single chemical step for preparing 3-methyl-tetrahydrofuran from alpha-methylene-gamma-butyrolactone.

BACKGROUND OF THE INVENTION

Substituted tetrahydrofuran, like 3-methyl-tetrahydrofuran of the present invention, is in general useful in those areas in which tetrahydrofuran is used. Examples include polymerization to obtain fibers and uses as a solvent.

Poly (tetra methylene ether glycol) is polymerized to produce tetrahydrofuran. This polymer is used as chain segments in polyurethanes and polyesters. Polyurethanes based on poly (tetra methylene ether glycol) soft-segment have improved hydrolytic stability, abrasion resistance and elastomeric properties. Other benefits include strength, toughness, durability, low compression set property, and high water vapor permeability. The largest end-use area of these polyurethanes is as spandex fibers for apparel. Products containing poly (tetra methylene ether glycol) are also used in wheels, high-speed rolls, automotive parts, bushings, specialty hose, cable sheathing and coating, pipeline liners, and roof and floor coatings. 3-methyl-tetrahydrofuran monomer can be utilized as a comonomer for modifying poly(tetra methylene ether glycol) to yield better elastomeric properties.

In use of tetrahydrofuran as a solvent where lower volatility is desired, 3-methyl-tetrahydrofuran is advantageous because tetrahydrofuran boils at 66° C. whereas 3-methyl-tetrahydrofuran boils at 86° C.

Processes for producing 3-methyl-tetrahydrofuran, by hydrogenation of an itaconic acid ester or a 3-formyl-2-methylpropionic acid ester, and by hydrogenation of a methyl-succinic ester are described in Japanese Patent Applications 219981/1994 and 217768/1996, respectively. Along with the objective 3-methyl-tetrahydrofuran, these reactions produce an alcohol, which has to be separated in a further step. The 3-methyl-tetrahydrofuran forms an azeotropic mixture with most of the lower alcohols, for example, with methanol having an azeotropic point at 64.5° C., and an azeotropic composition consisting of 25% by weight of 3-methyl-tetrahydrofuran and 75% by weight of methanol. The existence of this azeotrope necessitates a costly, energy intensive separation step to yield pure 3-methyl-tetrahydrofuran. In particular, the 3-methyl-tetrahydrofuran which is employed for modifying poly(tetramethylene glycol) can tolerate an alcohol impurity of less than 0.2%.

Similarly, U.S. Pat. No. 5,990,324 describes a process for producing 3-methyltetrahydrofuran by hydrogenation of beta-formylisobutyric acid ester with the general formula ROOC—CH(CH$_3$)—CH$_2$—CHO wherein, R is an alkyl group having 1 to 3 carbon atoms and the formyl group may be present as an acetal having an alkanol with 1 to 8 carbon atoms. In this process, the alcohol byproduct is separated from 2-methyl-gamma-butyrolactone in the second step. This separation can be effected by simple distillation. Although azeotropic distillation is not required, a separation of the alcohol remains a necessary step in the process of producing 3-methyl-tetrahydrofuran.

Alpha-methylene-gamma-butyrolactone is a reactive monomer. Direct catalytic conversion of alpha-methylene-gamma-butyrolactone to 3-methyl-tetrahydrofuran has been attempted in the past. But owing to the high temperature required for the catalytic reaction (greater than 150° C.), the conversion results in polymerization of the α-methylene-γ-butyrolactone.

Thus, the problem to be solved is to provide a simple, economical, one-step process for the production of 3-methyl-tetrahydrofuran. The one step process of the present invention describes a more efficient route to produce 3-methyl-tetrahydrofuran from α-methylene-γ-butyrolactone with novel catalyst systems, without any alcohol production, thereby eliminating the step of azeotropic or any other type of separation.

SUMMARY OF INVENTION

This invention relates to a chemical process for producing 3-methyl-tetrahydrofuran, which comprises the step of hydrogenating alpha-methylene-gamma-butyrolactone, represented by the compound of formula (I), to yield 3-methyl-tetrahydrofuran (II) as product, (in the presence of a catalytic metal).

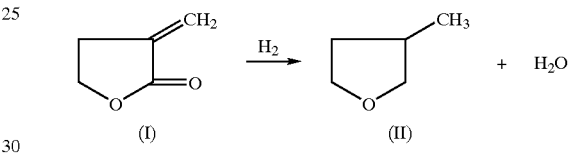

DETAILED DESCRIPTION OF THE INVENTION

By "alpha-methylene-gamma-butyrolactone" is meant the compound described by the formula below.

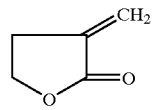

By "acid promoter" is meant a compound that is acidic in nature which is added to enhance the physical or chemical function of a catalyst.

By "metal promoter" is meant a metallic compound that is added to enhance the physical or chemical function of a catalyst.

The acid and metal promoters are chemical promoters generally used to augment the activity of catalyst agents. The promoter may be incorporated into the catalyst during any step in the chemical processing of the catalyst constituent.

This invention relates to the synthesis of 3-methyl-tetrahydrofuran from alpha-methylene-gamma-butyrolactone. More specifically, this invention relates to synthesis of 3-methyl tetrahydrofuran in a single chemical step process from alpha-methylene-gamma-butyrolactone. The chemical process does not generate alcohol as a side product. The final product does not need separation or purification of alcohol. Owing to the high temperature of the catalytic reactions (greater than 150° C.), previous attempts to directly convert alpha-methylene-gamma-butyrolactone to 3-methyl-tetrahydrofuran have resulted in the formation of a polymer of alpha-methylene-gamma-butyrolactone monomer.

The present method involves hydrogenation of alpha-methylene-gamma-butyrolactone to yield 3-methyl-tetrahydrofuran as product. A metal catalyst, with or without a support, may be present to effect the hydrogenation reaction. An acid material may optionally be used as a promoter to aid the reaction. A metal may also be optionally used as a promoter to aid the reaction.

The process of the present invention may be carried out in batch, sequential batch (i.e., a series of batch reactors) or continuous mode in any of the equipment customarily employed for continuous process. The condensate water is optionally removed from the reaction mass with the aid of an inert gas purge.

The temperature of the process is controlled in order to achieve a high yield of 3-methyl-tetrahydrofuran. A temperature range of from about 100° C. to about 250° is employed for the reaction. A temperature range of from about 200° C. to about 250° C. is preferred. A more preferred temperature range is from about 220° C. to about 230° C.

A pressure range of from about 3.4 MPa to about 14.0 MPa is employed in the reaction. Pressure range of from about 5.1 MPa to about 10.4 MPa is preferred. A more preferred pressure range is from about 5.1 MPa to about 6.9 MPa.

As used herein, a catalyst is a substance that affects the rate of the reaction but not the reaction equilibrium, and emerges from the process, chemically unchanged. A chemical promoter generally augments the activity of a catalyst. The promoter may be incorporated into the catalyst during any step in the chemical processing of the catalyst constituent. The chemical promoter generally enhances physical or chemical function of the catalyst agent, but they can also be added to retard undesirable side reactions.

Hydrogenation of alpha-methylene-gamma-butyrolactone to 3-methyl-tetrahydrofuran is effected in presence of a catalytic metal. The principal component of the catalyst is selected from the group consisting of palladium, ruthenium, rhenium, rhodium, iridium, platinum, compounds thereof, and combinations thereof.

The catalytic metal used in the process disclosed here may be used as a supported or as an unsupported catalyst. A supported catalyst is one which in which the active catalyst agent is deposited on a support material by spraying, soaking or physical mixing, followed by drying, calcination, and if necessary, activation through methods such as reduction or oxidation. Materials frequently used as support are porous solids with high total surface areas (external and internal) which can provide high concentrations of active sites per unit weight of catalyst. The catalyst support may enhance the function of the catalyst agent. A catalyst which is not supported on a catalyst support material is an unsupported catalyst. The support material is selected from the group consisting of carbon, alumina, silica, silica-alumina, titania, and a combination thereof. Moreover, supported catalytic metals may have the same supporting material or different supporting material. A preferred support is carbon. The carbon can be a commercially available carbon such as Calsicat C, Sibunit C, or Calgon C (under the trade name Centaur(R)).

A preferred catalytic metal content range in a supported catalyst is from about 0.1% to about 15%. A more preferred catalytic metal content range is from about 1% to about 7%. A further preferred catalytic metal content range is from about 1% to about 5%.

Preferred combinations of catalytic metal and support system includes palladium on carbon combined with rhenium on carbon, and rhodium on carbon combined with rhenium on carbon.

An acid promoter may be used in the reaction of the present invention. Suitable promoters include those acids with a pKa less than about 4, preferably with a pKa less than about 2, including inorganic acids, organic sulfonic acids, heteropolyacids, perfluoroalkylsulfonic acids, and mixtures thereof. Also suitable are metal salts of acids with pKa less than about 4, including metal sulfonates, metal trifluoroacetates, metal triflates, and mixtures thereof including mixtures of salts with their conjugate acids. Specific examples of promoters include sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluroethanesulfonic acid, 1,2,3,2,3,3-hexapropanesulfonic acid, bismuth triflate, yttrium triflate, ytterbium triflate, neodymium triflate, lanthanum triflate, scandium triflate, and zirconium triflate. A preferred promoter is selected from $Zn(BF_4)_2$, CBV-3020E zeolite, and 20 A zeolite. The acid promoter is used in concentration of from 0.1% to 5% by weight. A preferred concentration range is 0.25% to 2.5%.

Suitable heterogeneous acid promoters are zeolites, fluorinated alumina, acid-treated silica, acid treated silica-alumina, acid treated clays, heterogeneous heteropolyacids and sulfated zirconia.

A metal promoter may be used optionally with the acid promoter in the method of the present invention. Suitable metal promoters include tin, zinc, copper, gold, silver, and combinations thereof. A preferred metal promoter is tin.

Experimental

The following abbreviations are used in the Examples:

| | |
|---|---|
| ESCAT | Series of catalysts provided by Engelhard Corp. |
| Calsicat Carbon | Catalyst support from Engelhard Corp. |
| Sibunit Carbon | Catalyst support from Inst. of Technical Carbon, Omsk, Russia |
| JM-A11108 Carbon | Catalyst support from Johnson Matthey, Inc. |
| Calgon Carbon | Catalyst support from Calgon Corp. under the brand name of Centaur(R) |
| CBV-3020E | Type of Zeolite acid promoter |
| 20-A | Type of Zeolite acid promoter |

A commercially available support such as carbon, alumina, silica, silica-alumina, titania available from Engelhard Corp. (E. Windsor, Conn.) was impregnated by incipient wetness with a metal salt. The precursors used were $NiCl_2 \cdot 6H_2O$ (Alfa Chemical Co.), $Re_2O_7$ (Alfa Chemical Co.), $PdCl_2$(Alfa Chemical Co.), $RuCl_3 \cdot xH_2O$ (Aldrich Chemical Co.). $H_2PtCl_6$ (Johnson Matthey, W. Deptford, N.J.), $CrCl_3 \cdot 6H_2O$ (Mallinckrodt Baker, Inc.), 5% Rh using $RhCl_3 \cdot xH_2O$ (Alfa Chemical Co.). The samples were dried and reduced at 300–450° C. in $H_2$ for 2 hours.

The carbon used was commercially available as Calsicat Carbon, Sibunit Carbon, or Calgon Carbon (Centaur(R)). Calsicat Carbon is lot no. S-96-140 from Engelhard Corp, Beachwood, Ohio Sibunit Carbon is Sibunit-2 from Institute of Technical Carbon, 5th Kordnaya, Omsk 64418, Russia. Calgon Carbon is PCB Carbon from Calgon Corp. (under the registered trademark of Centaur(R)).

EXAMPLE-1

Catalyst Preparation

5%Pt on Acid Washed Calsicat Carbon

In a 150 ml beaker, a solution was made up of 4.5 ml, 0.3 M $H_2PtCl_6$ with 4.0 ml deionized $H_2O$. To the beaker were added 4.75 g Calsicat Acid Washed Carbon (12×20 mesh, dried at 120° C. overnight). The slurry was allowed to stand at room temperature for 1 hr with occasional stirring and then dried at 120° C. overnight with frequent stirring (until free flowing).

In an alumina boat, in a quartz lined tube furnace, the catalyst was purged with 500 SCCM $N_2$ at room temperature for 15 min and then with 100 SCCM He at room temperature for 15 min. The catalyst was heated to 150° C. and held at 150° C under He for 1 hr. At this point, 100 SCCM $H_2$ were added and the sample was held at 150° C. under He and $H_2$ for 1 hr. The temperature was increased to 300° C. and the catalyst was reduced at 300° C. under He—$H_2$ for 8 hrs. The $H_2$ was stopped, the sample was held at 300° C. under He for 30 min and then cooled to room temperature in flowing He. The catalyst was finally passivated in 1.5% $O_2$ in $N_2$ at 500 SCCM for 1 hour at room temperature and weighed 4.93 grams when unloaded.

EXAMPLES 1–36

HYDROGENATION OF ALPHA-METHYLENE-GAMMA-BUTYROLACTONE TO 3-METHYL-TETRAHYDROFURAN

50% MBL in Dioxane (1000.6 mg, 5.1 mmole), and an amount of catalyst and support as indicated in the table below, were added to a 2 ml pressure reactor. The reactor was sealed and charged with 6.89 MPa of $H_2$ and heated to reaction temperature of 225° C. The reaction was stopped after a determined period of time and cooled down in 10 to 15 minutes. An internal standard (2-methoxyethyl ether) was added into the reaction mixture and GC analysis was performed on a HP-6890 GC with a Chrompack column (CP-WAX 58,25 M×25 MM).

The following table lists the reaction conditions, catalyst, acid promoter and conversion and selectivity of the reactant and products, respectively. All experiments were conducted with a 50% alpha-methylene-gamma-butyrolactone in dioxane.

TABLE 1

| Ex. No. | Time (hrs) | Catalyst | Acid Promoter | MBL Conversion (%) | 3-Me-THF Selectivity (%) | MeGBL Selectivity (%) |
|---|---|---|---|---|---|---|
| 1. | 2 | 5% Pd/C(ESCAT 140) | | 99.21 | 0.23 | 83.53 |
| 2. | 2 | 5% Pd/C(ESCAT 142) | | 85.57 | 0.28 | 93.72 |
| 3. | 2 | 5% Pd/C(ESCAT 143) | | 99.49 | 0.19 | 96.94 |
| 4. | 2 | 5% Pd/C(ESCAT 148) | | 86.71 | 0.33 | 97.80 |
| 5. | 2 | 5% Pd/C(ESCAT 149) | | 99.92 | 0.14 | 94.36 |
| 6. | 2 | 5% Pd/C(ESCAT 160) | | 95.05 | 0.24 | 97.80 |
| 7. | 2 | 5% Pd/C(ESCAT 162) | | 97.87 | 0.15 | 88.55 |
| 8. | 2 | 1% Ru/6%Re/C | | 99.44 | 0.16 | 90.27 |
| 9. | 2 | 1% Ru/6%Re/C | Zn(BF4)2 | 91.31 | 0.57 | 63.14 |
| 10. | 2 | 1% Ru/6%Re/C | CBV-3020 | 94.25 | 0.87 | 71.79 |
| 11. | 2 | 1% Ru/6%Re/C | 20A | 93.15 | 1.05 | 64.49 |
| 12. | 2 | 1.87%Ru/5.65%Re/0.77%Sn/C | Zn(BF4)2 | 78.25 | 0.46 | 51.03 |
| 13. | 2 | 1.87%Ru/5.65%Re/0.77%Sn/C | CBV-3020 | 96.76 | 0.06 | 1.14 |
| 14. | 4 | 5%Pd/C JM-A11108-5 + 5%Re/Sibunit C | | 100.00 | 1.68 | 95.62 |
| 15. | 4 | 5%Pd/C JM-A11108-5 + 5%Re/Calsicat C | | 100.00 | 2.58 | 95.43 |
| 16. | 4 | 5%Pd/C JM-A11108-5 + 5%Re/Calgon C | | 100.00 | 0.59 | 61.23 |
| 17. | 4 | 5%Pd/C JM-A11108-5 + 5%Re/Calsicat C(400C) | | 100.00 | 1.94 | 94.34 |
| 18. | 4 | 5%Pd/C JM-A11108-5 + 10%Re/Calsicat C(400C) | | 100.00 | 3.33 | 94.79 |
| 19. | 4 | 5%Pd/C + 20%Re/Calsicat C(400C) | | 100.00 | 5.10 | 93.84 |
| 20. | 4 | 5%Pd/C JM-A11108-5 + 5%Re/Sibunit C | | 100.00 | 8.22 | 90.04 |
| 21. | 4 | 5%Pd/C JM-A11108-5 + 5%Re/Calsicat C | | 100.00 | 12.66 | 82.70 |
| 22. | 4 | 5%Pd/C JM-A11108-5 + 5%Re/Calgon C | | 100.00 | 2.93 | 92.38 |
| 23. | 4 | 5%Pd/C JM-A11108-5 + 5%Re/Calsicat C(400C) | | 100.00 | 10.14 | 85.15 |
| 24. | 4 | 5%Pd/C JM-A11108-5 + 10%Re/Calsicat C(400C) | | 100.00 | 12.35 | 83.89 |
| 25. | 4 | 5%Pd/Calsicat C + 5%Ir/Calsicat C | | 100.00 | 1.25 | 89.34 |
| 26. | 4 | 5%Rh/Calsicat C + 5%Ir/Calsicat C | | 100.00 | 1.84 | 87.45 |
| 27. | 4 | 5%Ru/Calsicat C + 5%Ir/Calsicat C | | 100.00 | 2.91 | 81.53 |
| 28. | 4 | 5%Ru/Al2O3 + 5%Ir/Calsicat C | | 98.41 | 0.51 | 80.21 |
| 29. | 4 | 5%Pd/Calsicat C − 5%Ir/Al2O3 | | 100.00 | 0.67 | 90.74 |
| 30. | 4 | 5%Rh/Calsicat C + 5%Ir/Al2O3 | | 100.00 | 0.55 | 86.61 |
| 31. | 4 | 5%Ru/Calsicat C + 5%Ir/Al2O3 | | 98.50 | 0.51 | 62.70 |

TABLE 1-continued

| Ex. No. | Time (hrs) | Catalyst | Acid Promoter | MBL Conversion (%) | 3-Me-THF Selectivity (%) | MeGBL Selectivity (%) |
|---|---|---|---|---|---|---|
| 32. | 4 | 5%Ru/Al2O3 5%Ir/Al2O3 | | 98.33 | 0.17 | 68.52 |
| 33. | 4 | 5%Pd/Calsicat C + 5%Re/Cal. C | | 98.74 | 5.96 | 77.39 |
| 34. | 4 | 5%Rh/Calsicat C + 5%Re/Cal. C | | 99.63 | 21.42 | 60.41 |
| 35. | 4 | 5%Ru/Calsicat C + 5%Re/Cal. C | | 86.95 | 5.58 | 55.00 |
| 36. | 4 | 5%Ru/Al2O3 5%Re/Cal. C | | 94.14 | 5.56 | 68.68 |

What is claimed is:

1. A process for producing 3-methyl-tetrahydrofuran represented by formula (II), comprising hydrogenating the compound alpha-methylene-gamma-butyrolactone, represented by the formula (I) in the presence of a catalytic metal.

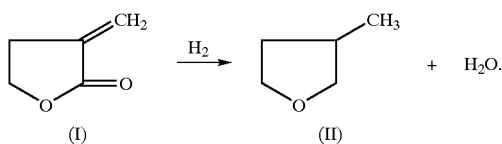

2. The process as recited in claim 1, wherein the catalytic metal is selected from the group consisting of palladium, ruthenium, rhenium, rhodium, iridium, platinum, compounds thereof, and combinations thereof.

3. The process as recited in claim 1, wherein the catalytic metal is supported on a catalyst support.

4. The process as recited in claim 3, wherein the catalyst support is selected from the group consisting of carbon, alumina, silica, silica-alumina, titania, compounds thereof, and combinations thereof.

5. The process as recited in claim 1, wherein the reaction is effected in the presence of a metal promoter.

6. The process as recited in claim 5, wherein the metal promoter is selected from the group consisting of tin, zinc, copper, gold, silver, and combinations thereof.

7. The process as recited in claim 5, wherein the metal promoter is tin.

8. The process as recited in claim 1, wherein the reaction is effected in the presence of acid promoter.

9. The process as recited in claim 8, wherein the acid promoter is an acid with a pKa less than about 4, or a metal salt thereof.

10. The process as recited in claim 9, wherein the acid promoter is selected from the group consisting of inorganic acids, organic sulfonic acids, heteropolyacids, perfluoroalkyl sulfonic acids, and metal salts thereof.

11. The process as recited in claim 10, wherein the acid promoter is selected from the group consisting of sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluorethanesulfonic acid, 1,1,1,2,3,4-hexafluorpropanesulfonic acid, bismuth triflate, yttrium triflate, ytterbium triflate, neodymium triflate, lanthanum triflate, scandium triflate, and zirconium triflate.

12. The process as recited in claim 8, wherein the acid promoter is selected from the group consisting of zeolites, fluorinated alumina, sulfuric acid-treated silica, sulfuric acid-treated silica-alumina, heteropolyacids supported on zirconia, titania, alumina, and/or silica.

13. The process as recited in claim 8, wherein the acid promoter is $Zn(BF_4)_2$.

14. The process as recited in claim 8, wherein the acid promoter is zeolite CBV-3020E.

15. The process as recited in claim 8, wherein the acid promoter is zeolite CBV-20A.

16. The process as recited in claim 1, wherein the reaction is effected in the presence of an acid promoter and a metal promoter.

17. The process as recited in claim 1, wherein the process is performed at a temperature from about 100° C. to about 250° C.

18. The process as recited in claim 1, wherein the process is performed at a temperature from about 200° C. to about 250° C.

19. The process as recited in claim 1, wherein the process is performed at a temperature from about 220° C. to about 230° C.

20. The process as recited in claim 1, wherein the process is performed at a pressure from about 3.4 MPa to about 14.0 MPa.

21. The process as recited in claim 1, wherein the process is performed at a pressure from about 5.1 MPa to about 10.4 MPa.

22. The process as recited in claim 1, wherein the process is performed at a pressure from about 5.1 MPa to about 6.9 MPa.

23. The process as recited in claim 1, wherein the process is performed at a temperature from about 220° C. to about 230° C., and a pressure from about 5.1 MPa to about 6.9 MPa.

24. The process as recited in claim 1, wherein the catalytic metal is supported and the catalytic metal support is palladium on carbon combined with rhenium on carbon.

25. The process as recited in claim 1, wherein the catalytic metal is supported and the catalytic metal support is rhodium on carbon combined with rhenium on carbon.

26. The process as recited in claim 24, wherein the palladium on carbon is present in an amount of 5% by weight of the catalytic metal support and the rhenium on carbon is present in an amount of 5% by weight of the catalytic metal support.

27. The process as recited in claim 24, wherein the palladium on carbon is present in an amount of 5% by weight of the catalytic metal support and the rhenium on carbon is present in an amount of 10% by weight of the catalytic metal support.

28. The process as recited in claim 25, wherein the rhodium on carbon is present in an amount of 5% by weight of the catalytic metal support and the rhenium on carbon is present in an amount of 5% by weight of the catalytic metal support.

29. The process as recited in claim 25, wherein the rhodium on carbon is present in an amount of 5% by weight of the catalytic metal support and the rhenium on carbon is present in an amount of 10% by weight of the catalytic metal support.

* * * * *